(12) United States Patent
Benita et al.

(10) Patent No.: US 6,656,460 B2
(45) Date of Patent: Dec. 2, 2003

(54) METHOD AND COMPOSITION FOR DRY EYE TREATMENT

(75) Inventors: Simon Benita, Mevaseret Zion (IL); Gregory Lambert, Verrieres le Buisson (FR)

(73) Assignees: Yissum Research Development, Jerusalem (IL); Company of the Hebrew University of Jerusalem Novagali S.A.S., Evry (FR)

( * ) Notice: Subject to any disclaimer, the term of this patent is extended or adjusted under 35 U.S.C. 154(b) by 44 days.

(21) Appl. No.: 09/985,185

(22) Filed: Nov. 1, 2001

(65) Prior Publication Data

US 2003/0108626 A1 Jun. 12, 2003

(51) Int. Cl.$^7$ ............................................. A61K 31/74
(52) U.S. Cl. ................................... 424/78.04; 514/912
(58) Field of Search ....................... 424/78.04; 514/912

(56) References Cited

U.S. PATENT DOCUMENTS

| | | | |
|---|---|---|---|
| 4,421,748 A | 12/1983 | Trager et al. |
| 4,894,366 A | 1/1990 | Okuhara et al. |
| 4,914,088 A | 4/1990 | Glonek et al. |
| 5,106,615 A | 4/1992 | Dikstein |
| 5,278,151 A | 1/1994 | Korb et al. |
| 5,294,607 A | * 3/1994 | Glonek et al. |
| 5,371,108 A | 12/1994 | Korb et al. |
| 5,578,586 A | 11/1996 | Glonek et al. |
| 6,007,826 A | 12/1999 | Benita et al. |

FOREIGN PATENT DOCUMENTS

| | | |
|---|---|---|
| WO | WO 93/18852 | 9/1993 |
| WO | WO 95/31211 A1 | 11/1995 |
| WO | WO 02/09667 A2 | 2/2002 |

OTHER PUBLICATIONS

Abdulrazik et al; "Effect of Emulsion Droplet Surface Charge on Cyclosporine Ocular Tissue Distribution"; vol. 42, No. 4, Mar. 15, 2001; p. S925 XP008005391; Abstract.

Klang et al; "Physiochemical Characterization and Acute Toxicity Evaluation of a Positively–Charged Submicron Emulsion Vehicle"; *Journal of Pharmacy and Pharmacology*; vol. 46, No. 12, 1994, pp. 986–993. XP–008005426.

Klang et al; "Evaluation of a Positively Charged Submicron Emulsion of Piroxicam on the Rabbit Corneum Healing Process Following Alkali Burn"; *Journal of Controlled Release*; vol. 57, No. 1, 1999, pp. 19–27; XP004155636.

Klang et al; "Influence of Emulsion Droplet Surface Charge on Indomethacin Ocular Tissue Distribution"; *Pharmaceutical Development and Technology*; vol. 5, No. 4, 2000, pp. 521–532; XP008005503.

Elbaz et al; "Positively Charged Submicron Emulsions—A New Type of Colloidal Drug Carrier"; *International Journal of Pharmaceutics*, vol. 96, 1993, R1–R6.

M. Y. Levy et al; "Interactions of a Non–ionic Surfactant with Mixed Phospholipid–oleic acid monolayers. Studies under dynamic conditions"; *Colloids and Surfaces*; vol. 59, 1991, pp. 225–241.

S. Muchtar et al; :Penetration of Amphoteric Surfactants into phospholipid monolayers spread at the air—water interface; *Colloids and Surfaces B: Biointerfaces*; vol. 1, 1993, pp. 149–155.

S. Davis, "The Stability of fat emulsions for intravenous administration; *Current Perspectives In The Use of Lipid Emulsion*"; Chapter 5.

S. C. Yang et al; "Enhanced Absorption and Drug Targeting by Positively Charged Submicron Emulsions"; *Drug Development Research*; vol. 50, pp. 476–486, 2000.

* cited by examiner

*Primary Examiner*—Carlos Azpuru
(74) *Attorney, Agent, or Firm*—Browdy and Neimark, P.L.L.C.

(57) ABSTRACT

A method and composition for treating a dry eye condition by topically applying to the eye surfaces an emulsion forming a tear film that acts to lubricate the eye and to inhibit evaporation therefrom. The emulsion is constituted by water in which is dispersed a mixture that includes a phospholipid, a non-polar oil, a non-toxic emulsifying agent and a polar lipid that imparts a net positive charge to the film that is distributed throughout the film, causing the film to be electrostatically attracted to the anionic surface of the eye whereby the film adheres thereto and cannot be washed away. Includable in the mixture is a non-soluble therapeutic agent, such as cyclosporin which is effective against an eye disease and is delivered to the eye by the film.

15 Claims, No Drawings

METHOD AND COMPOSITION FOR DRY EYE TREATMENT

BACKGROUND OF THE INVENTION

1. Field of the Invention

This invention relates generally to the treatment of a dry eye condition, and in particular to a method and composition for this purpose which forms an artificial tear film on the surface of the eye acting to inhibit evaporation therefrom and delivering to the eye surface an efficacious medicament to treat an eye disease.

2. Status of Prior Art

The main concern of the present invention is with the treatment of a dry eye condition by a method and composition that acts to lubricate the eye and to reduce evaporation of fluid from the cornea surface. The cornea normally functions to maintain this surface in a moist and lubricated state which is impaired when the eye suffers from a dry eye condition.

Dehydration of moisture from the eye gives rise to various discomforts such an ocular dryness as well as burning and scratching sensations. But the more serious consequence of a dry eye condition is a loss of visual acuity which if it persists and is not corrected, may result in permanent damage. Dry eye disease acts to degrade the exposed ocular surface and may cause a complete breakdown of corneal tissues. In an extreme case, this may necessitate a corneal transplant.

Symptoms accompanying a dry eye condition are exacerbated when the eye is covered by a contact lens. The rate of evaporation of liquid from the eye is accelerated by the contact lens whose presence results in a meniscii formation that promotes evaporation even when the eye has an adequate natural tear film.

The usual treatment prescribed for a dry eye condition is to alleviate its symptoms by the topical application of a tear film substitute that adds a substantial volume of liquid to the anterior surface of the eye. A typical composition functioning as a tear film substitute includes soluble polymer solutions. Of prior art interest in this regard is the U.S. Pat. No. 4,421,740 to Trager which discloses an artificial tear composition formed by an aqueous hypotonic solution of lecithin, a phospholipid, and a viscosity-adjusting agent.

Of particular prior art interest are the following U.S. patents in each of which Korb is a co-inventor. Hence these patents will hereinafter be referred to as Korb patents:

I. U.S. Pat. No. 4,914,088 (1990)
II. U.S. Pat. No. 5,278,151 (1994)
III. U.S. Pat. No. 5,371,108 (1994)
IV. U.S. Pat. No. 5,294,607 (1994)

The Korb patents point out that a normal eye has an ocular surface coated with a tear film composed of:

(a) a mucous inner layer in contact with the ocular surface of the eye
(b) an aqueous middle layer which is the source of moisture, and
(c) a lipid outer layer which minimizes evaporation of the moisture from the film.

"Dry eye" is experienced when the outer layer (c) of the tear film is defective. The dry eye treatment disclosed and claimed in Patents I to IV involves the topical application to the eye of phospholipids which form an artificial film over the eye that replicates a normal outer lipid layer and maintains the eye in moist condition.

Patent I is directed to an artificial tear film formed by:
"a layer of a complex phospholipid having a net positive or negative charge".

According to this Korb patent, the significance of a net positive or negative net charge is that in either case, the charged molecules in the film coating the surface of the eye "repel each other" and in doing so, maintain "the integrity of the phospholipid therein" so that it acts "as a barrier reducing evaporation." Hence it is a negative or positive repelling charge that the inventor regards to be the crux of his invention.

Patent I fails to take into account that the surface of the eye being treated is anionic and therefore will interact electrostatically with a charged coating in a way that depends on the polarity of the charge. According to Patent I, the polarity of the charge doesn't matter, for in either polarity the charged molecules in the film repel each other.

An important aspect of the present invention is not only that it has a positive net charge, but also that the strength and distribution of the charge is such as to cause the film to adhere electrostatically to the entire anionically-charged eye surface to provide an effective moisture barrier. A weak positive charge would not achieve this result. Inasmuch as in present invention, the positively-charged molecules in the film covering the eye surface electrostatically engage the negatively-charged molecules on this surface, the resultant electrostatic couple is neutral and the couples do not repel each other.

Korb patent II discloses an eye treatment composition comprising

"a layer of a complex phospholipid having a net charge" and
"a layer of an essentially non-polar oil over said phospholipid layer", the phospholipid and oil layers being in an amount "below that amount that would result in significant prolonged blurring of vision".

According to Patent II, the preferred phospholipids are those "carrying a net negative charge because the negatively-charged molecules would be repelled by the negatively-charged ocular surface, thereby permitting the maintenance of a relatively thick aqueous layer".

In contradistinction, the present invention which resides in a positively-charged composition, exploits the fact that the eye surface is negatively charged (anionic) so that the composition is electrostatically attracted to this surface to create a coating which prevents the escape of moisture from the eye surface for a prolonged retention period.

Korb patent III also discloses a composition in which the phospholipid has a net negative or positive charge causing molecules in the tear film coating the eye surface to repel each other to maintain the integrity of the film. In Korb patent IV, the eye treated composition is a mixture of a charged phospholipid and a non-polar oil in a meta-stable water emulsion.

Essential to the present invention is that the emulsion coating the eye surface to form a film thereon carries a net positive charge which is distributed uniformly throughout the film so that it is electrostatically attracted to the entire anionic eye surface whereby the molecules on the film surface do not repel each other but are attracted to the eye surface.

Also of particular prior art interest is PCT patent publication WO 95/31211 (Nov. 25, 1995) of Allergan, Inc. This publication discloses an emulsion for topical application to ocular tissue which includes cyclosporin admixed with castor oil. As noted in this publication, cyclosporin comprises a group of cyclic oligopeptides, the major component of which is cyclosporin A ($C_{62}H_{111}N_{11}O_{12}$), Clyclosporin has been found to be effective in the treatment of a dry eye condition.

SUMMARY OF THE INVENTION

In view of the foregoing, the main object of this invention is to provide an improved method and composition for treating a dry eye condition by topically applying to the eye surface an emulsion forming a tear film that adheres electrostatically to the entire surface of the eye and acts to lubricate the eye and to inhibit evaporation of moisture therefrom.

Among the significant advantages of a method and composition in accordance with the invention are the following:

A. The tear film derived from the emulsion caries a strong net positive charge that is uniformly distributed throughout the film surface whereby the film is electrostatically attracted to the entire area of the negatively-charged eye surface and there is no uncoated zone.

B. The electrostatic attraction between the artificial tear film and the eye surface maintains adhesive contact therebetween for a prolonged retention period and the tear film cannot be readily washed away.

C. The tear film coating the eye surface has no adverse effects, for the film includes no toxic or other harmful agents.

Also an object of this invention is to provide a composition of the above type which incorporates therein a therapeutic agent for treating an eye disease, such as cyclosporin A which when the composition is topically applied then delivers the agent to the eye. The release of the agent from the coating film to the surface of the eye is maintained for a prolonged period in that the film is held electrostatically in contact therewith.

Briefly stated, these objects are attained in a method and composition for treating a dry eye condition by topically applying to the eye surfaces an emulsion forming a tear film that acts to lubricate the eye and to inhibit evaporation therefrom. The emulsion is constituted by water in which is dispersed a mixture that includes a phospholipid, a non-polar oil and a polar lipid that imparts a net positive charge to the film that is distributed throughout the film, causing the film to be electrostatically attracted to the anionic surface of the eye whereby the film adheres to the eye and cannot be washed away. Includable in the mixture is a non-soluble therapeutic agent such as cyclosporin which is effective against an eye disease and is delivered to the eye by the film.

DETAILED DESCRIPTION OF THE INVENTION

Cyclosporin A (CsA), a lipid-soluble cyclic endecapeptide, is a potent and well established immunomodulator drug mainly for oral use. With oral formulations, CsA bioavailability is limited because of the drug's insolubility in water and its tendency to separate immediately as a solid after coming into contact with water. Moreover, the bioavailability is highly dependent on complex interactions occurring between the formulation and the physiological environment of the lumen.

CsA has been found to be effective in treating the immune-mediated keratoconjunctivitis sicca (KCS or dry eye disease) by the enhancement or restoration of lachrymal gland tearing in patient suffering from this syndrome. Dry eye disease is characterized by chronic drying of the conjunctiva and cornea, as well as by decreased tear production and changes in the composition of the tear film. In order to enhance the efficiency of CsA treatment, it becomes necessary to increase the absorption of the drug in the lachrymal gland as well as the conjunctiva and cornea target tissues, using for the purpose a suitable dosage of the drug to suppress ocular inflammation without significant systemic CsA exposure.

Since the aqueous solubility of CsA is between about 20 to 30 $\mu$g/ml, there is no adequate aqueous formulations available for ocular administration of the drug. Moreover, if cyclosporin is administered orally for the treatment of KCS, the accompanying side effects due to systemic circulation may cause adverse reactions such as hypertrichosis or renal dysfunction. In addition, the concentration of CsA present in oral formulations is limited due to the drug's hydrophobic nature.

Studies on ocular CsA penetration in animals were carried out using CsA formulations based on olive oil and corn oil. Local toxic effects on the cornea attributable to topical CsA formulations or the intrinsic solvent were observed. Upon using CsA in olive oil, in an ex vivo examination on bovine cornea, histological study revealed that the corneal epithelium was keratinized with some necrotic cells and rare pyonotic nuclei. Moreover, several researchers have confirmed that the probable toxic effect was due to topically administered CsA dissolved in olive oil. The conclusion reached is that olive oil, rather than CsA was responsible for the surface epithelial defects developing in the cornea. Hence, because of its high hydrophobicity, it is necessary to formulate CsA with compatible vehicles. These are not always biocompatible with ophthalmic administration, and may present some problems of stability such as the rancidity of olive oil. The drawback of corn-oil concentrated ointment formulations is that they may exacerbate the symptoms (early-burning, redness and itching) of a dry eye condition.

It is possible to minimize problems related to unpleasant sensations and syndrome exacerbation by reducing the oil content and dispersing the oil phase in a water phase, resulting in an emulsion. We have found that when castor oil is used in developing the emulsion dosage, there are additional benefits to patients with dry eye disease arising from the long ocular retention time of the emulsion vehicle. The castor oil droplets in the emulsion form a lipid layer over the tear film, reducing the evaporation of the limited natural tears produced while the emulsion remains in the eye of a patient.

Our investigation of a positively-charged submicron emulsion containing a phospholipid having Zeta potential values ranging from 34–45 mV and a mean droplet size of around 150–250 nm supports the significant advantages which are gained when the emulsion vehicle carries a net-positive charge, rather than either a negative or neutral charge.

The resultant electrostatic attraction between the positively-charged submicron oil droplets in the emulsion and the corneal eye surface, which is negatively-charged results in a more prolonged residence or retention time conducive to topical drug flux enhancement.

Hence a positively-charged submicron emulsion of CsA enhances the local concentration of this medicament in conjunctiva and cornea which are the target ocular tissues. A positively-charged emulsion in accordance with the invention is therefore far more efficacious therapeutically than a negative charge emulsion having a similar composition.

The Composition The following represent formulations for a composition in accordance with the invention for treating a dry eye condition and other eye diseases.

Formulation (1) is a positive blank emulsion to be applied topically to an eye surface to create on the surface an artificial tear film. Formulation (2) which is for a CsA positive emulsion has the same ingredients as formulation (1), to which is added cyclosporin. The resultant film serves as a vehicle to deliver the medicament to the eye surface.

| Cyclosporin A | 0.00 | 0.20 |
| --- | --- | --- |
| Castor oil | 2.50 | 2.50 |
| LIPOID E-80 (Lipoid Co.), a mixture of phospholipids comprising mainly 80% phosphatidylcholine, 8% phosphatidylethanolamine 3.6% non-polar lipids, and about 2% sphingomyelin | 0.50 | 0.50 |
| Stearylamine | 0.12 | 0.12 |
| Vitamin E | 0.01 | 0.01 |
| Pluronic F-68 | 0.42 | 0.42 |
| Glycerol | 2.25 | 2.25 |
| Benzalkouium chloride | 0.01 | 0.01 |
| Distilled water to | 100.00 | 100.00 |

Lipid E-8 is a non-polar phospholipid, stearylamine is a cationic lipid and therefore imparts to the emulsion which also includes a non-polar castor oil a net positive charge. Pluronic F-68 is the trademark for poloxamer 188, a polyoxyalkyline derived from polypropylene glycol. Poloxamer 188 is an emulsifying agent and the glycerol in the formulation functions as an osmotic agent. Benzalkonium chloride is a cationic surfactant antiseptic agent acting as a preservative of the emulsion and strengthening the positive charge imparted to the emulsion by the cationic lipid. Vitamin E acts as a lipophillic antioxidant and as an eye lubricant.

In practice a composition may include instead of the cationic lipid stearylamine, cationic lipid oleylamine. The relative percentages of the ingredients included in the composition are not limited to those set forth above. Thus the relative percentage of castor oil may be in the range of 0.5 to 10%, that of the phospholipid LIPOID E-80 (Lipoid Co.) a mixture of phospholipids comprising mainly 80% phosphatidyloholine, 8% phosphatidylethanolamine, 3.6% non-polar lipids, and about 2% sphingomyelin) in the range of 0.1 to 2.0%, that of the cationic lipid in the range of 0.1 to 0.5%, and that of the emulsifying agent, (Pluronic F-68), in the range of 0.5 to 2.0%.

It is vital however that whatever are the relative ranges of these ingredients, that the emulsion carry a net positive charge of sufficient strength to cause the emulsion when forming a film on the anionic surface of an eye, that it be electrostatically attracted to the surface so that it adheres thereto and cannot be readily washed away.

LIPOID E80 (Lipoid Co.), a mixture of phospholipids comprising mainly 80% phosphatidylcholine, 8% phosphatidylethanolamine, 3.6% non-polar lipids, and about 2% sphingomyelin, Pluronic F-68 and stearylamine coact to improve the stability of the emulsion droplets which are preferably in the submicron range, by enhancing the mechanical strength of the interfacial films formed around the droplets.

It is important to bear in mind that in a composition in accordance with the invention which is to be administered topically to the anionic surface of an eye, that the phospholipid and castor oil included in the formulation carry no charge and that the aggregate net positive charge imparted to the submicron droplets is derived from the cationic surfactant plus the cationic antiseptic agent.

The advantage of this formulation over a dry eye treatment composition in which the charge imparted to the droplets is derived only from the phospholipid, as in the Korb patents, is that with the present formulation the positive charge of the emulsion is uniformly distributed over the entire area of the artificial tear film which is produced when the emulsion coats the anionic surface of the eye.

This results in electrostatic attraction throughout the entire area of the eye surface so that no portion thereof remains uncoated and untreated. Hence the present invention affords a treatment for a dry eye condition in which evaporation moisture is inhibited over the entire eye surface and no moisture is permitted to escape therefrom.

Preparation of Composition

Poloxamer 188 (Pluronic F-68) the osmotic agent (glycerol), and benzalkonium chloride were dissolved in the aqueous phase. The lipid E-80 is first dissolved in ethanol (1:5) and then dispersed in the aqueous phase. The ethanol is evaporated during the heating process of the aqueous phase. An antioxidant ($\alpha$-tocopherol), the cationic lipid stearylamine (or oleylamine) and the CsA were dissolved in the castor oil phase. Both phases were heated separately to 70° C. The water phase was slowly incorporated into the oily phase and mixed with a magnetic stirrer. The resulting mixture was further heated to a temperature of 85° C.

The coarse emulsion obtained was emulsified for 5 minutes, using a high shear Polytron mixer and then rapidly cooled to below 20° C. After cooling in an ice bath, the emulsion was homogenized using a two stage homogenizer valve assembly for 5 minutes. After further rapid cooling below 20° C., the pH was adjusted to 7.0 using 0.1 N hydrochloric acid. The emulsion was then filtered through a TE membrane filter (Schleicher & Schuell, Dassel, Germany) with a pore size of 0.45 $\mu$m. Finally, the emulsion was packed under nitrogen atmosphere in siliconized glass bottles and then sterilized by autoclaving at 121° C. for 15 minutes, It is desirable that the droplets of the emulsion be in the submicron range and it is vital that the emulsion which is to be applied topically to the eye surface be sterile.

Medicaments: In an emulsion in accordance with the invention which is to be applied topically to the surface of an eye to treat a dry eye condition can also function as a vehicle to deliver a therapeutic agent to the eye to treat an eye disease.

The common practice in treating an eye infection is to deposit drops of an antibiotic agent in the eye, the number of drops to be applied on any one occasion being prescribed by a physician. Since this number defines the dosage of the drug applied to the eye, one must be careful that the drops are limited to the eye and that none of the applied liquid escapes therefrom. But in practice, it is difficult to deposit a drop of liquid into the eye so that none of the liquid flows beyond the eye borders, for there is little to hold the liquid to the eye surface.

The advantage of using an emulsion in accordance with the invention as a vehicle to deliver a therapeutic agent to the eye is that the emulsion which coats the entire surface of the eye and spreads the agent over its anionic surface, adheres electrostatically to this surface so that all of the therapeutic agent in a predetermined dosage is delivered to the eye. And because the coating electrostatically adheres to the eye surface and cannot be washed away, the residence time of treatment is prolonged and the therapeutic agent is therefore more effective.

The fact that the droplets in the charged emulsion in accordance with the invention are of submicron size is significant. This results in a much greater charge density per unit area of the emulsion film than would be produced had the droplet size been in the micron range and therefore produces a more powerful electrostatic force.

We have in the foregoing disclosed cyclosporin A as a preferred medicament to be incorporated in the emulsion. But other water-insoluble medicaments may be used provided that they possess properties for the treatment of eye disease similar to those of cyclosporin and are non-polar. Should the medicament carry a negative charge, then the amount of the cationic ingredient included in the emulsion must be such as to provide a net positive charge.

Thus among suitable medicaments that can be incorporated in an emulsion in accordance with the invention are those in the family of compounds including tacrolimus disclosed in U.S. Pat. No. 4,894,366. Also suitable is Sirolimus (Rapamycin) disclosed in U.S. Pat. No. 3,993,749.

While there has been disclosed preferred embodiments of the invention, it is to be understood that many changes may be made therein without departing from the spirit of the invention.

What is claimed is:

1. A method of treating a dry eye condition comprising:
   preparing an emulsion in which water has dispersed therein a mixture including a non-polar phospholipid, a non-polar oil, a non-toxic emulsifying agent, and a cationic lipid which imparts to the emulsion a net positive charge; and
   topically applying the emulsion to an eye surface to form a tear film which is electrostatically attracted to the anionic surface of the eye whereby the film adheres to the surface; wherein the emulsion is prepared to create submicron droplets thereof.

2. A method of treating a dry eye condition comprising:
   preparing an emulsion in which water has dispersed therein a mixture including a non-polar phospholipid, a non-polar oil, a non-toxic emulsifying agent, a water-insoluble medicament, and a cationic lipid which imparts to the emulsion a net positive charge; and
   topically applying the emulsion to an eye surface to form a tear film which is electrostatically attracted to the anionic surface of the eye whereby the film adheres to the surface.

3. A method according to claim 1, in which the phospholipid is Lipoid E-80, a mixture of phospholipids comprising: mainly 80% phosphatidylochline, 8% phosphatidylethanolamine, 3.6% non polar lipids and about 2% sphingomyelin.

4. A method according to claim 1, in which the cationic lipid is stearylamine.

5. A method according to claim 1, in which the cationic lipid is oleylamine.

6. A method according to claim 1, in which the relative percentage of the phospholipid in the emulsion lies in the range of 0.1 to 0.5 percent.

7. A method according to claim 1, in which included in the mixture is vitamin E.

8. A method according to claim 1, in which the emulsifying agent is poloxamer.

9. A method according to claim 1, in which the relative percentage of the emulsifying agent in the emulsion lies in the range of 0.5 to 2.0 percent.

10. A method according to claim 1, wherein the mixture further includes a cationic antiseptic agent.

11. A method according to claim 1, in which the antiseptic agent is benzalkonium chloride.

12. A method according to claim 1, in which the mixture further includes a water-insoluble medicament to treat eye disease.

13. A method according to claim 12, in which the medicament is cyclosporin.

14. A method according to claim 12, in which the medicament is tacrolimus.

15. A method according to claim 12, in which the medicament is sirolimus.

* * * * *